United States Patent
Shiraki et al.

(10) Patent No.: US 9,638,657 B2
(45) Date of Patent: May 2, 2017

(54) SENSOR AND METHOD FOR REMOVING INTERFERING SUBSTANCE

(71) Applicant: ARKRAY, Inc., Kyoto (JP)

(72) Inventors: Yasunori Shiraki, Kyoto (JP); Koji Katsuki, Kyoto (JP); Kazuya Iketani, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/990,990

(22) Filed: Jan. 8, 2016

(65) Prior Publication Data

US 2016/0123917 A1 May 5, 2016

Related U.S. Application Data

(62) Division of application No. 13/641,022, filed as application No. PCT/JP2011/057641 on Mar. 28, 2011, now Pat. No. 9,271,671.

(30) Foreign Application Priority Data

Apr. 16, 2010 (JP) ................................. 2010-095387

(51) Int. Cl.
*G01N 27/327* (2006.01)
*A61B 5/1473* (2006.01)
(Continued)

(52) U.S. Cl.
CPC ..... *G01N 27/3274* (2013.01); *A61B 5/14735* (2013.01); *A61B 5/14865* (2013.01);
(Continued)

(58) Field of Classification Search
CPC ............ G01N 27/3274; A61B 5/14735; A61B 5/14865
See application file for complete search history.

(56) References Cited

U.S. PATENT DOCUMENTS

| 4,772,375 A | 9/1988 | Wullschleger et al. |
| 5,384,029 A | 1/1995 | Campbell |

(Continued)

FOREIGN PATENT DOCUMENTS

| EP | 0207370 A2 | 7/1987 |
| EP | 0396156 A1 | 11/1990 |

(Continued)

OTHER PUBLICATIONS

Greco ed., Implantation Biology: The Host Response and Biomedical Devices, CRC Press, pp. 68-80 (1994).

(Continued)

*Primary Examiner* — Paul West
(74) *Attorney, Agent, or Firm* — Morgan, Lewis & Bockius LLP

(57) ABSTRACT

A technique is provided, wherein any influence, which would be otherwise exerted on a reaction of an objective substance caused by a reagent enzyme by an interfering substance contained in a specimen, is suppressed in relation to an electrochemical sensor for measuring the objective substance contained in the specimen. A sensor comprises a substrate; a detecting unit which is provided on the substrate and which detects an objective substance; a filter which covers the detecting unit, which permits permeation of the objective substance on one hand, and which regulates permeation of an interfering substance contained in a sample on the other hand; and removing unit which removes the interfering substance adhered to the filter.

13 Claims, 9 Drawing Sheets

(51) Int. Cl.
*A61B 5/1486* (2006.01)
*A61B 5/00* (2006.01)
*G01N 1/34* (2006.01)
*G01N 27/40* (2006.01)
*C25F 1/00* (2006.01)

(52) U.S. Cl.
CPC .......... *A61B 5/6848* (2013.01); *A61B 5/6865* (2013.01); *C25F 1/00* (2013.01); *G01N 1/34* (2013.01); *G01N 27/3272* (2013.01); *G01N 27/40* (2013.01)

(56) References Cited

U.S. PATENT DOCUMENTS

| | | |
|---|---|---|
| 5,776,324 A | 7/1998 | Usala |
| 6,001,067 A | 12/1999 | Shults et al. |
| 6,030,827 A | 2/2000 | Davis et al. |
| 6,343,225 B1 | 1/2002 | Clark |
| 7,153,265 B2 | 12/2006 | Vachon |
| 7,471,972 B2 | 12/2008 | Rhodes et al. |
| 2003/0000833 A1 | 1/2003 | Mansouri et al. |
| 2005/0054909 A1 | 3/2005 | Petisce et al. |
| 2008/0319296 A1 | 12/2008 | Bernstein et al. |
| 2010/0056894 A1 | 3/2010 | Cote et al. |

FOREIGN PATENT DOCUMENTS

| | | |
|---|---|---|
| JP | 62-005169 A | 1/1987 |
| JP | 11-513914 A | 11/1999 |
| JP | 2002-501195 A | 1/2002 |
| JP | 2003-513230 A | 4/2003 |
| JP | 2006-126046 A | 5/2006 |
| JP | 2007-511737 A | 5/2007 |
| JP | 2008-256725 A | 10/2008 |
| JP | 4295615 B2 | 7/2009 |
| WO | 97/43633 A1 | 11/1997 |
| WO | 99/38003 A1 | 7/1999 |
| WO | 01/20019 A2 | 3/2001 |
| WO | 03/011131 A2 | 2/2003 |
| WO | 2005/011520 A2 | 2/2005 |
| WO | 2008/107649 A1 | 9/2008 |
| WO | 2008/124597 A1 | 10/2008 |
| WO | 2008/157821 A1 | 12/2008 |

OTHER PUBLICATIONS

International Search Report issued for corresponding International Application No. PCT/JP2011/057641 dated Jun. 14, 2011.

International Preliminary Report on Patentability and Written Opinion issued in corresponding International Patent Application No. PCT/JP2011/057641 dated Nov. 6, 2012.

Extended European Search Report issued in European Patent Application No. 11768714.5 dated Jul. 10, 2014.

Office Action issued in related U.S. Appl. No. 14/991,018 dated Mar. 11, 2016.

Office Action issued in corresponding U.S. Appl. No. 14/991,018 dated Sep. 22, 2016.

SENSOR AND METHOD FOR REMOVING INTERFERING SUBSTANCE

TECHNICAL FIELD

The present invention relates to a sensor for measuring an objective substance contained in a sample, and a method for removing an interfering substance adhered to the sensor.

BACKGROUND ART

An electrochemical sensor is known, for example, as a sensor for measuring an objective substance (specified component) contained in a sample. The electrochemical sensor is the sensor which is capable of detecting a minute amount of current by utilizing an electrochemical reaction. In the case of a glucose sensor of the subcutaneous retention type (to be retained subcutaneously beneath the skin), when glucose molecules, which exist in a specimen or sample, arrive at the enzyme developed on an electrode, glucose is oxidized in accordance with the enzymatic reaction. It is possible to estimate the concentration of glucose in a body fluid on the basis of a response current signal obtained by electrochemically oxidizing hydrogen peroxide ($H_2O_2$) which is produced during this process. The sample is exemplified, for example, by an intercellular fluid which exists extracellularly in the subcutaneous tissue. The method, in which the response current obtained by allowing glucose contained in a sample to react together with a reagent enzyme (for example, glucose oxidase (GOD), glucose dehydrogenase (GDH) or the like) provided on a measuring sensor as described above, is referred to as "enzyme electrode method". Further, a sensor is also known, which adopts such an optical detecting method (referred to as "colorimetric method" in some cases) that the intensity is measured at a color developing wavelength while previously applying a color developing reagent enzyme (for example, hexokinase (HK) or the like) which specifically causes a reaction of an objective substance contained in a sample.

In this specification, a part or region, which is provided on a substrate of a measuring sensor and which is provided to detect an objective substance contained in a sample, is referred to as "detecting unit". For example, the reaction reagent is retained in the detecting unit. The body fluid contains, for example, microorganisms (for example, bacteria and fungi), protein, fibrin, and lipid in addition to glucose as the objective substance. For example, when the microorganism exists around the detecting unit (for example, an electrode of a glucose sensor), it is feared that the measurement accuracy may be deteriorated by destroying the enzyme developed on the electrode and/or consuming, for example, glucose, oxygen or the like. In relation thereto, such a technique has been suggested that an antifungal agent, an antibiotic or the like is previously mixed with the enzyme (see, for example, Patent Document 1).

On the other hand, if the subcutaneous retention period is prolonged, then protein, fibrin and the like gradually adhere to the electrode, and the formation of foreign body capsule (FBC) is induced. Finally, matured FBC such as vascular fibrous tissue is formed (see, for example, Non-Patent Document 1). If such a situation arises, for example, glucose hardly arrives at the electrode. It is feared that any influence may be exerted on the measurement of the glucose concentration. In relation thereto, a biosensor has been also suggested, comprising a first film which is a porous film for covering an electrode and which has an electron donor region formed on a surface thereof for allowing protein and fibrin to easily adhere, and a second film which is combined with the electron donor region of the first film and which has a bonding hydrogen atom donor composed of phenyl ring (see, for example, Patent Document 2).

PRECEDING TECHNICAL DOCUMENTS

Patent Documents

Patent Document 1: JP2003-513230A
Patent Document 2: JP11-513914A

Non-Patent Document

Non-Patent Document 1: Inflammation and Biomaterials in Greco R S, ed. Implantation Biology: the Host Response and Biomedical Devices, pp 68-80, CRC Press (1994).

SUMMARY OF THE INVENTION

Task to be Solved by the Invention

The substance, which includes, for example, the microorganism, protein, fibrin, and lipid as described above, is the interfering substance which interferes in (exerts any influence on) the reaction of the objective substance caused by the enzyme on the glucose sensor. It is considered that the effect may be lowered as the time elapses, even when any countermeasure is adopted, for example, such that an agent such as an antifungal agent, an antibiotic or the like is previously mixed with the enzyme and/or an agent is retained by a film for covering the enzyme in order not to allow the interfering substance to adhere to the enzyme, wherein there is room for improvement.

The present invention has been made taking the forgoing actual circumstances into consideration, an object of which is to provide such a technique that any harmful influence is suppressed, which would be otherwise exerted on the detection of an objective substance in a detecting unit by an interfering substance contained in a sample, in relation to a sensor for measuring the objective substance contained in the sample.

Solution for the Task

In order to solve the problem as described above, the present invention adopts the following means. That is, the present invention resides in a sensor for measuring an objective substance contained in a sample; the sensor comprising a substrate; a detecting unit which is provided on the substrate and which detects the objective substance; a filter which covers the detecting unit, which permits permeation of the objective substance on one hand, and which regulates permeation of an interfering substance contained in the sample on the other hand; and a removing unit which removes the interfering substance adhered to the filter. The sensor according to the present invention may be, for example, an electrochemical sensor provided with the detecting unit including a reagent enzyme retained on an electrode provided on the substrate. The interfering substance, which is referred to in the present invention, is the substance which interferes in (exerts any influence on) the detection of the objective substance performed by the detecting unit. For example, when the reagent enzyme, which causes the reaction of the objective substance, is retained in the detecting unit, any substance or the like, which interferes in the reaction of the objective substance caused by the reagent enzyme, can be exemplified as the interfering substance.

According to the present invention, the interfering substance is not transmitted (permeated) through the filter. Therefore, the interfering substance does not arrive at the detecting unit. For example, when the subcutaneous retention period lasts for a long period of time, the interfering substance, which is contained in the sample, is gradually adhered and accumulated (deposited) on the filter. If the adhesion amount (accumulation amount) of the interfering substance is excessively increased on the filter, for example, the filter is completely clogged up. As a result, any smooth arrival of the objective substance at the detecting unit (including, for example, the reagent enzyme retained on the detecting unit) is inhibited.

On the contrary, in the present invention, the interfering substance, which adheres to the surface of the filter, can be removed from the filter in a state in which the filter is exposed to the sample. For example, the process for removing the interfering substance as described above is executed at every certain periods or on the basis of the monitoring result of the response current signal generated by an electrochemical sensor when the sensor according to the present invention is the electrochemical sensor. Thus, it is possible to suppress any excessive increase in the adhesion amount of the interfering substance adhered to the filter. In other words, the interfering substance can be removed before the adhesion amount of the interfering substance is excessively increased. Therefore, according to the present invention, it is possible to suppress any harmful influence which would be otherwise exerted by the interfering substance contained in the sample on the detection of the objective substance performed by the detecting unit. Accordingly, it is also possible to suppress the deterioration of the measurement accuracy of the objective substance to be measured by the sensor.

The removing unit, which is provided for the sensor of the present invention, may remove the interfering substance adhered to the filter by vibrating the filter. In this case, for example, the removing unit may be constructed to include a piezoelectric element which is vibrated by applying a voltage; and vibration transmitting unit which is fixed to the piezoelectric element and which transmits vibrational energy of the piezoelectric element to the filter. Accordingly, the interfering substance, which adheres to the filter, can be appropriately removed from the filter.

The removing unit, which is provided for the sensor of the present invention, may remove the interfering substance adhered to the filter by supplying, to the filter, an agent for decomposing the interfering substance. In this case, for example, the removing unit may be constructed to include a piezoelectric element which is vibrated by applying a voltage; an accommodating case which accommodates the agent; and a discharge hole which is formed to be open on the accommodating case; and the agent may be discharged from the discharge hole by transmitting vibrational energy of the piezoelectric element to the accommodating case so that the agent is supplied to the filter. In this arrangement, when the piezoelectric element is vibrated, the vibrational energy is transmitted to the accommodating case, and thus the agent, which is accommodated in the accommodating case, is discharged form the discharge hole to the filter. Accordingly, the interfering substance, which adheres to the filter, can be appropriately removed from the filter.

The removing unit, which is provided for the sensor of the present invention, may be constructed to have at least a pair of removing electrodes which are arranged in mutual contact with the filter or closely to the filter; and the interfering substance adhered to the filter may be removed by means of electrolytic cleaning for the removing electrodes performed by applying a voltage between the removing electrodes. Accordingly, the interfering substance, which adheres to the filter, can be appropriately removed from the filter. In this case, the removing electrodes may be arranged so that the interfering substance, which adheres to the removing electrodes and the filter, is formed while being joined or linked together.

In the sensor according to the present invention as described above, the detecting unit may be used while being retained subcutaneously.

In order to solve the problem as described above, the present invention can be also grasped from an aspect of a method for removing the interfering substance. In particular, the present invention resides in a method for removing an interfering substance, to be applied to a sensor comprising a detecting unit which is provided on a substrate and which detects an objective substance contained in a sample; the method comprising allowing the interfering substance to adhere to a filter beforehand by covering the detecting unit with the filter which permits permeation of the objective substance on one hand and which regulates permeation of the interfering substance contained in the sample on the other hand, and removing the interfering substance adhered to the filter by means of removing unit which removes the interfering substance. According to this removing method, the interfering substance, which adheres to the filter, can be appropriately removed from the filter.

The foregoing method for removing the interfering substance according to the present invention can be applied to any one of the sensors as described above. Further, the means for solving the problem according to the present invention can be combined with each other as far as possible.

Effect of the Invention

According to the present invention, it is possible to suppress any harmful influence which would be otherwise exerted by the interfering substance contained in the sample on the detection of the objective substance performed by the detecting unit in the sensor for measuring the objective substance contained in the sample.

MODE FOR CARRYING OUT THE INVENTION

Figure 1:
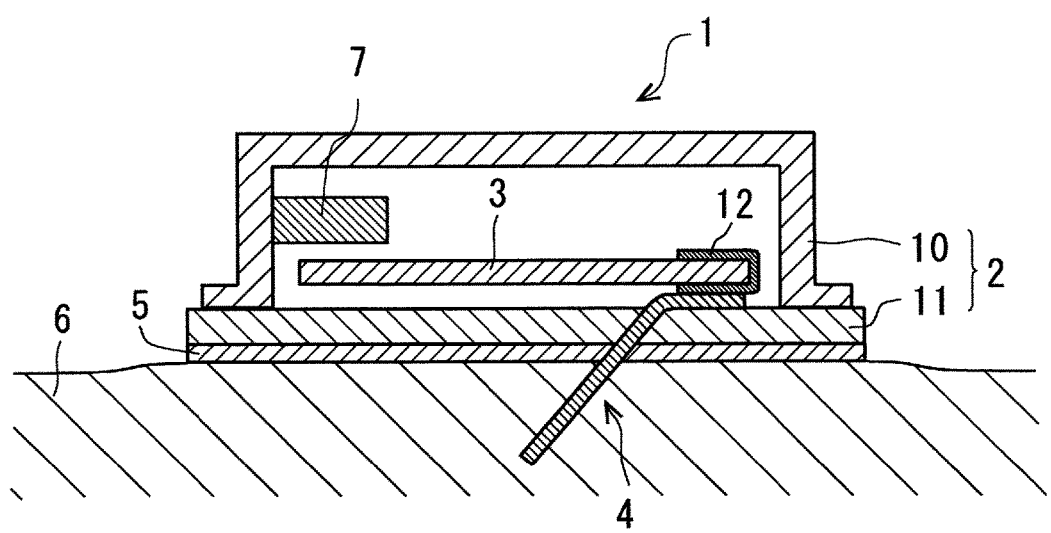
FIG. 1 shows a schematic arrangement of a component continuous measuring apparatus provided with an electrochemical sensor according to a first embodiment.

The sensor according to the present invention will be explained below with reference to the drawings. The sensor according to the mode for carrying out the present invention will be explained as exemplified by an electrochemical sensor for measuring an objective substance by utilizing the electrochemical reaction by way of example. The structures or arrangements of the following embodiments are described by way of example. The electrochemical sensor according to the mode for carrying out the present invention is not limited to the structures or arrangements of the embodiments. For example, the sizes or dimensions, the materials, the shapes, and the relative arrangement of the constitutive elements in the respective embodiments are not intended to limit the technical scope of the invention only thereto, unless otherwise specifically noted. In the following drawings, the components or parts, which are the same as or equivalent to the components or parts depicted in the preceding drawings, are designated by the same reference numerals. The explanation of the respective embodiments of the sensor according to the present invention described below also serves as the explanation of the respective embodiments of the method for removing the interfering substance applied to the sensor according to the present invention.

First Embodiment

A first embodiment of the electrochemical sensor according to the mode for carrying out the present invention will be explained. FIG. 1 shows a schematic arrangement of a component continuous measuring apparatus 1 provided with an electrochemical sensor according to the first embodiment. The component continuous measuring apparatus 1 shown in FIG. 1 can continuously measure the concentration of a specified objective substance (specified objective component) contained in a sample. The sample includes, for example, blood and intercellular fluid. The specified objective substance includes, for example, glucose, lactic acid, and bile acid. The component continuous measuring apparatus 1 can be used while being attached to a human body. The component continuous measuring apparatus 1 is provided with a casing 2, a circuit board 3, and an electrochemical sensor 4. In the following embodiment, an explanation will be exemplarily made about such a case that glucose, which is contained in the intercellular fluid, is used as the objective as the specified objective substance.

The casing 2 includes a cover 10 and a main body substrate 11. The circuit board 3 is accommodated in the space defined by the cover 10 and the main body substrate 11. It is preferable that the casing 2 has the waterproof property or the water resistant property. Materials, which have extremely low water permeability as exemplified, for example, by metal and polypropylene resin, may be used for the cover 10 and the main body substrate 11.

The main body substrate 11 is a portion through which the electrochemical sensor 4 is inserted. The main body substrate 11 fixes a part of the electrochemical sensor 4. An adhesive film 5 is fixed to the main body substrate 11. The adhesive film 5 is utilized when the component continuous measuring apparatus 1 is fixed to the skin 6. For example, a tape, which has stickiness on both surfaces, can be used as the adhesive film 5.

The circuit board 3 carries electronic parts necessary for predetermined operations of the component continuous measuring apparatus 1 (for example, application of the voltage, calculation of the concentration of the specified objective substance, and communication with any external apparatus). The circuit board 3 is provided with terminals 12 for making electric connection with respect to the electrochemical sensor 4. The terminals 12 are utilized to apply the voltage to the electrochemical sensor 4 and obtain the response current value from the electrochemical sensor 4.

The electrochemical sensor 4 is the sensor to obtain the response corresponding to the concentration of the specified component contained in the specimen, i.e., glucose contained in the intercellular fluid in this case. A part of the electrochemical sensor 4 protrudes from the skin 6, which is brought in contact with the terminals 12 of the circuit board 3. Further, another part of the electrochemical sensor 4 is inserted while being implanted into the skin 6. That is, the electrochemical sensor 4 is used while a part thereof is retained in the skin 6 (subcutaneously beneath the skin).

Figure 2:
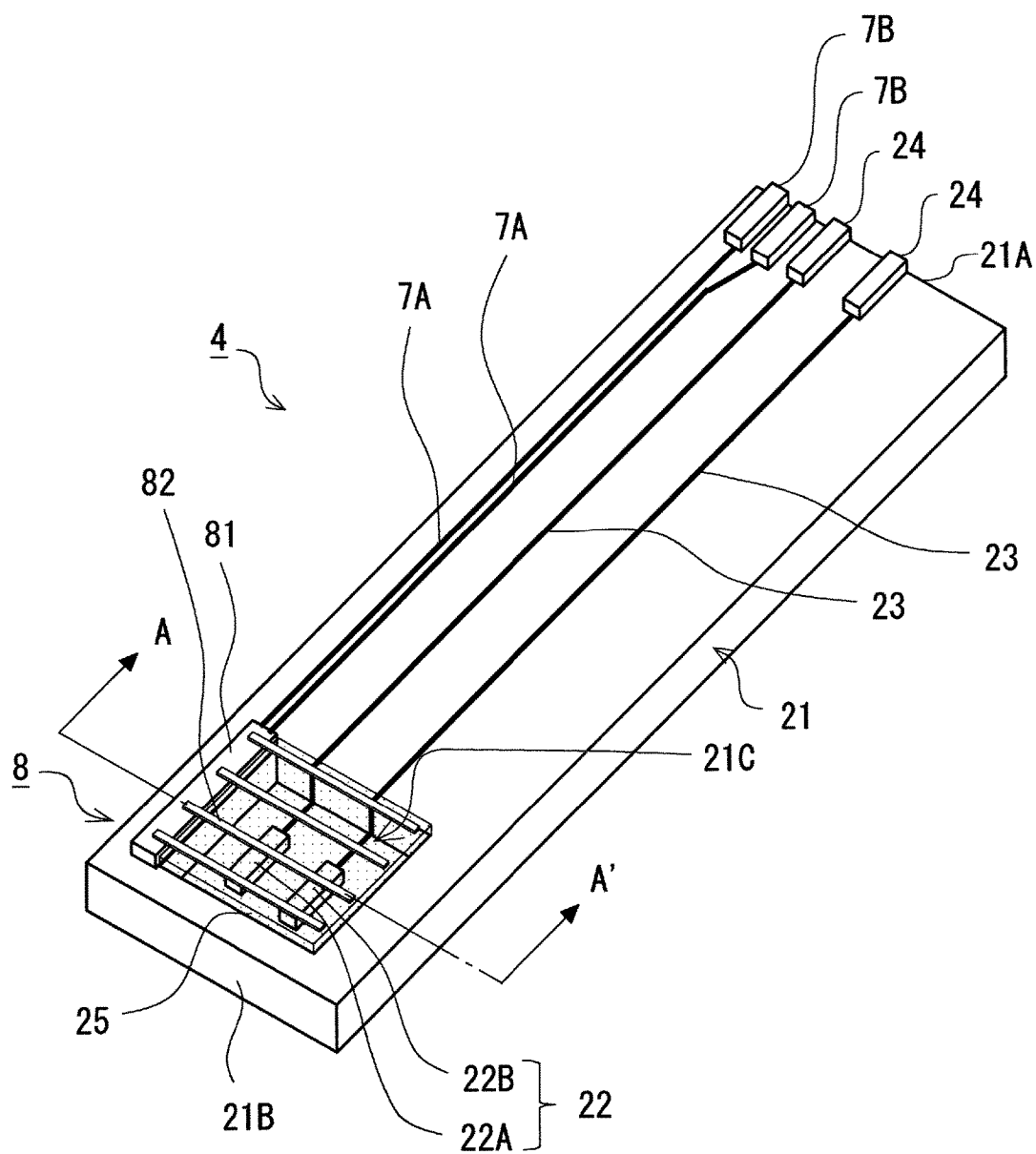
FIG. 2 shows a perspective view illustrating the entire electrochemical sensor according to the first embodiment.

FIG. 2 shows a perspective view illustrating the entire electrochemical sensor 4 according to the first embodiment. The electrochemical sensor 4 has a sensor substrate 21, a detecting unit 22, lead wires 23, terminals 24, and a filter 25.

The sensor substrate 21 has the insulating property and the flexibility, and the sensor substrate 21 supports the detecting unit 22. A part of the sensor substrate 21, which includes an end portion 21A, is accommodated in the casing 2. Another part of the sensor substrate 21, which includes an end portion 21B disposed on the side opposite to the end portion 21A, is inserted into the skin 6. The end portion 21B of the sensor substrate 21 may have a sharp shape. When the end portion 21B of the sensor substrate 21 has the sharp shape, then the electrochemical sensor 4 can be easily inserted into the skin 6, and it is possible to reduce the pain of an objective person into which the electrochemical sensor 4 is inserted.

A material, which has the biocompatibility and the insulating property, can be used for the sensor substrate 21. It is possible to use, for example, a resin such as polypropylene, polyimide, polyethylene terephthalate, polyether ether ketone, polyethylene naphthalate or the like for the sensor substrate 21. In the following description, the longitudinal direction of the sensor substrate 21 is the direction which is directed from the end portion 21B of the sensor substrate 21 to the end portion 21A of the sensor substrate 21 (direction in which the sensor substrate 21 is accommodated in the casing 2) or the direction which is directed from the end portion 21A of the sensor substrate 21 to the end portion 21B of the sensor substrate 21 (direction in which the sensor substrate 21 is inserted into the skin 6). The widthwise direction of the sensor substrate 21 is the direction which is perpendicular to the longitudinal direction of the sensor substrate 21. As for the sensor substrate 21, the end portion 21A is also referred to as "forward end portion 21A", and the end portion 21B is also referred to as "proximal end portion 21B".

A recess 21C is formed on the forward end side of the sensor substrate 21, and the detecting unit 22 is provided on the surface of the recess 21C. The detecting unit 22 can be formed, for example, by means of the vapor deposition, the sputtering, the printing (for example, the screen printing, the gravure printing or the like), or the transfer printing. The detecting unit 22 includes a working electrode 22A and a counter electrode 22B. The working electrode 22A is the portion to give and receive electrons with respect to the specified objective substance contained in a sample or specimen. The counter electrode 22B is utilized to apply the voltage together with the working electrode 22A.

One end portion of each of the lead wires 23 is connected to each of the working electrode 22A and the counter electrode 22B. Each of the terminals 24 is connected to the other end of each of the lead wires 23. The terminals 24 are brought in contact with the terminals 12 of the circuit board 3.

The reagent enzyme is formed on (for example, applied to) the surface of the working electrode 22A. In this embodiment, the concentration of glucose contained in a specimen is measured by using the electrochemical sensor 4. Therefore, glucose oxidase (GOD), which uses glucose as the substrate, is adopted as the reagent enzyme. Glucose dehydrogenase (GDH) may be adopted as the reagent enzyme in place of glucose oxidase. For example, when the concentration of lactic acid contained in a specimen is measured, it is possible to use lactate oxidase as the reagent enzyme. As for the method for immobilizing the reagent enzyme, it is possible to adopt various known methods including, for example, methods to utilize polymerizable gel; high molecular weight compound such as polyacrylamide, phosphorus or the like; MPC polymer including silane coupling agent introduced into phospholipid polymer; and protein film.

As shown in the drawing, the filter 25 is provided on the sensor substrate 21 so that the working electrode 22A and the counter electrode 22B are covered therewith. In particular, the filter 25 is provided so that the entire recess 21C formed on the sensor substrate 21 is covered therewith and the upper end opening is closed thereby. When the electrochemical sensor 4 is inserted into the skin 6, the detecting unit 22 is not directly brought in contact with the skin 6, because the filter 25 is provided so that the detecting unit 22 is covered therewith. In this way, the filter 25 also functions as the protective film for protecting the detecting unit 22.

When the intercellular fluid, which is permeated into the filter 25, arrives at the surface of the working electrode 22A, glucose oxidase, which is immobilized on the surface of the working electrode 22A, causes the reaction of glucose. The voltage is applied to glucose oxidase by means of the working electrode 22A and the counter electrode 22B, and thus the electrons are given and received between the working electrode 22A and glucose contained in the intercellular fluid.

That is, glucose contained in the intercellular fluid is reduced (electrons are taken out) by the aid of glucose oxidase immobilized on the working electrode 22A in the detecting unit 22, and the electrons are supplied to the working electrode 22A. The amount of electrons supplied to the working electrode 22A is measured as the response current value. As a result, an electric signal, which indicates the response current value as obtained when the voltage is applied, is generated by the electrochemical sensor 4, and the electric signal is inputted into the circuit board 3 of the component continuous measuring apparatus 1. The electric signal, which indicates the response current value, is the electric signal which correlates with the glucose concentration. The circuit board 3 calculates the glucose concentration (blood glucose level or blood sugar level) on the basis of the response current value. The result of calculation of the glucose concentration is transmitted to an external information terminal, if necessary.

Next, an explanation will be made in detail about the filter 25 and the structure or arrangement relevant to the filter 25.

The filter 25 is the member having such function that the permeation into the interior of the recess 21C is permitted for glucose as the specified objective substance on one hand, the permeation is regulated (permeation is prohibited) for the interfering substance that interferes in the reaction of glucose caused by glucose oxidase as the reagent enzyme, i.e., the enzymatic reaction of glucose oxidase on the other hand, and the interfering substance is collected.

The interfering substance includes, for example, microorganisms (for example, bacteria and fungi), protein, fibrin, and lipid contained in the specimen. If the microorganism exists around the detecting unit 22, then glucose oxidase is destroyed by the microorganism, and/or glucose and oxygen are consumed. The enzymatic reaction of glucose oxidase is affected thereby. If the protein and/or fibrin adhere/adheres to the detecting unit 22, glucose hardly arrives at the detecting unit 22, for example, due to the formation of the foreign body capsule (FBC) as described above. The enzymatic reaction of glucose oxidase is also affected thereby. If such a situation arises, for example, it is feared that the measurement accuracy of the glucose concentration may be consequently deteriorated. In view of the above, the interfering substance, which includes, for example, the protein and the microorganism contained in the specimen, is filtrated by the filter 25 so that the interfering substance is prevented from arriving at the detecting unit 22 to which glucose oxidase is immobilized.

The electrochemical sensor 4 of this embodiment is of the so-called subcutaneous retention type. The measurement duration period is set so that the glucose concentration is continuously measured for a relatively long period of time. For example, the measurement duration period lasts for several weeks in some cases. When the subcutaneous retention period of the electrochemical sensor 4 lasts for a long period of time as described above, then the amount of collection of the interfering substance collected by the filter 25, i.e., the amount of adhesion (amount of accumulation) of the interfering substance on the filter 25 is excessively increased, and it is feared that the filter 25 may be, for example, consequently clogged up. As a result, it is feared that the smooth arrival of glucose may be inhibited with respect to glucose oxidase retained on the working electrode 22A of the detecting unit 22. In view of the above, the electrochemical sensor 4 removes the interfering substance adhered to the filter 25 by means of an interfering substance removing unit 8 explained below. The interfering substance is removed by the interfering substance removing unit 8 in a state in which the filter 25 is exposed to the specimen (intercellular fluid), i.e., during the subcutaneous retention period in which the electrochemical sensor 4 is subcutaneously retained beneath the skin. The method for removing the interfering substance adhered to the electrochemical sensor 4 according to the present invention has the following feature. That is, the method comprises allowing the interfering substance to adhere to the filter 25 beforehand by covering the detecting unit 22 with the filter 25, and removing the interfering substance adhered to the filter 25 by means of the interfering substance removing unit 8 which removes the interfering substance.

A material, which has the biocompatibility, can be used for the filter 25. As for the filter 25, it is possible to use, for example, polyurethane, silicone-based polymer (polysiloxane), cellulose acetate, hydrogel, polyvinyl alcohol, HEMA (hydroxyethyl methacrylate), and copolymer containing any one of them. The filter 25 can be formed, for example, by means of the spin coat, the dip coat, or the drop coat.

Figure 3:
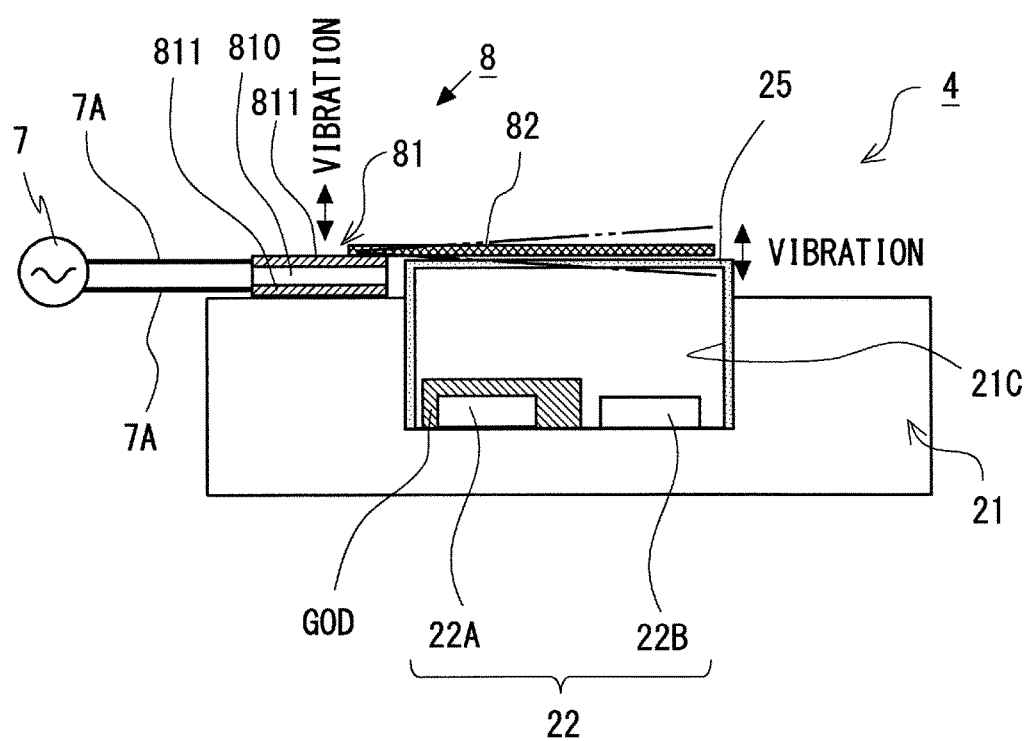
FIG. 3 shows a sectional view taken along a line A-A' indicated by arrows shown in FIG. 2.

An explanation will be made below with reference to FIGS. 2 and 3 about the detailed structure or arrangement of the interfering substance removing unit 8 according to the first embodiment. FIG. 3 shows a sectional view taken along a line A-A' indicated by arrows shown in FIG. 2. This sectional view shows a cross-sectional structure as obtained when the recess 21C of the sensor substrate 21 is cut or sectioned in the widthwise direction.

The interfering substance removing unit 8 removes the interfering substance accumulated or deposited on the filter 25, by vibrating the filter 25. The interfering substance removing unit 8 is constructed to include a piezoelectric element (piezo-element) 81 and vibration transmitting members 82. The piezoelectric element 81 is provided on the sensor substrate 21. In the example shown in FIG. 2, the shape of the upper end opening, which is provided for the recess 21C, is rectangular. The piezoelectric element 81 is arranged at a position disposed closely to the filter 25 along one upper end opening edge of the recess 21C. The piezoelectric element 81 is constructed by a piezoelectric member 810 which is deformable by applying a voltage, and two electrodes 811 which are connected to interpose the piezoelectric member 810 therebetween. The piezoelectric element 810 is a well-known element, and hence any detailed explanation thereof is omitted. In this specification, the direction, which is perpendicular to both of the longitudinal direction and the widthwise direction of the sensor substrate 21 (i.e., the direction perpendicular to the in-plane direction of the sensor substrate 21), is defined as "upward-downward direction".

An AC power source 7, which is provided to apply the AC voltage to the piezoelectric element 81, is accommodated in the casing 2 of the component continuous measuring apparatus 1. The electrodes 811, 811 of the piezoelectric element 81 are connected to the AC power source 7 via lead wires 7A and terminals 7B. The lead wires 7A and the AC power source 7 shown in FIG. 3 are schematically depicted in relation to the electric connection with respect to the piezoelectric element 81. The AC power source 7 is capable of performing the output, for example, within a range of ±0.2 V to ±24 V for the voltage and a range of 0.001 Hz to 1000 MHz for the frequency. However, these numerical ranges are provided by way of example.

When the AC voltage is applied from the AC power source 7 to the piezoelectric element 81, the piezoelectric element 81 is vibrated by periodically repeating the expanding/contracting deformation. As shown in FIG. 3, the electrodes 811 are stuck to the upper and lower surfaces of the piezoelectric member 810. Therefore, the piezoelectric element 81 repeats the expanding/contracting deformation in the upward-downward direction. The control, which relates to the voltage application by the AC power source 7, is performed by the circuit board 3 of the component continuous measuring apparatus 1.

In this context, the phenomenon, in which the electric polarization is induced by applying the force to a crystal in a certain specified direction to generate the positive and negative electric charges, is referred to as "piezoelectric effect". The phenomenon, in which the strain is generated in proportion to the voltage when the voltage is applied to a certain crystal, is referred to as "inverse piezoelectric effect". In the embodiment according to the present invention, the inverse piezoelectric effect is utilized. When the electric field is applied in parallel to the polarization direction, then the rotational force is generated in electric dipoles which are aligned on a straight line, the change in length is generated in the single crystal thereby, and the strong torque is consequently generated. For example, lead zirconate titanate (Pb(Zr,Ti)O3) is preferably employed as the material to be used for the piezoelectric member 810, which is generally abbreviated and referred to as PZT (piezo). The filter 25 is vibrated by the aid of the vibration transmitting members 82 as described later on by utilizing the torque and the length change of the piezoelectric member 810 generated by applying the voltage between the electrodes 811. Accordingly, it is possible to remove the interfering substance adhered to the filter 25.

The vibration transmitting member 82 is the member which is connected to the piezoelectric element 81 and which transmits the vibrational energy of the piezoelectric element 81 to the filter 25. As shown in the drawing, the vibration transmitting member 82 is the slender plate-shaped member constructed to have one end which is fixed to the piezoelectric element 81 and the other end which behaves as a free end. The vibration transmitting members 82 are arranged along the upper surface of the filter 25. When the vibration transmitting member 82 is vibrated in the upward-downward direction shown in FIG. 2 in cooperation with the expanding/contracting deformation of the piezoelectric element 81, the vibration transmitting member 82 collides with the filter 25 when the vibration transmitting member 82 is displaced in the direction to make approach to the filter 25 (alternate long and two short dashes line shown in FIG. 3 schematically illustrates the situation of vibration of the vibration transmitting member 82). Accordingly, the vibrational energy of the piezoelectric element 81 is transmitted to the filter 25, and the interfering substance, which is accumulated on the filter 25, is exfoliated from the filter 25 by the impact exerted thereby.

The vibration transmitting member 82 may be arranged in such a mode that the vibration transmitting member 82 is always brought in contact with the filter 25. The vibration transmitting member 82 may be fixed to the lower surface other than the upper surface of the piezoelectric element 81. In a more specified mode, for example, the vibration transmitting member 82 may be interposed between the lower surface of the piezoelectric element 81 and the sensor substrate 21. In any case, when the vibration transmitting member 82 is vibrated, then the vibrational energy is transmitted to the filter 25, and the interfering substance, which is adhered to the filter 25, is appropriately removed. In this embodiment, the vibrational energy of the piezoelectric element 81 is transmitted to the filter 25 by the aid of the vibration transmitting member 82. However, the piezoelectric element 81 may directly vibrate the filter 25.

As described above, when the interfering substance removing unit 8 is operated by the voltage applied from the AC power source 7, it is possible to remove the interfering substance adhered to the filter 25 which is in the state of being exposed to the specimen. Therefore, even when the subcutaneous retention period of the electrochemical sensor 4 lasts for a long period of time, the amount of adhesion (amount of accumulation) of the interfering substance to the filter 25 is suppressed from being excessively increased, for example, by periodically performing the process for removing the interfering substance. Thus, it is possible to secure the smooth reaction of glucose as the specified objective substance caused by the reagent enzyme. In other words, when the glucose concentration is measured, it is possible to suppress the influence which would be otherwise exerted by the interfering substance contained in the sample on the reaction of glucose caused by the reagent enzyme.

The control (hereinafter referred to as "interfering substance removing control"), under which the interfering substance accumulated on the filter 25 is removed, may be carried out at every constant periods during the measurement duration period for measuring the glucose concentration. As a result, it is possible to suppress the excessive increase in the amount of adhesion of the interfering substance to the filter 25. It is also preferable to carry out the interfering substance removing control when any sign or indication, which indicates that glucose hardly arrives at the detecting unit 22, is found from the change or transition of the calculation result of the glucose concentration. The execution timing of the interfering substance removing control referred to in this section is applicable to other embodiments and modified embodiments described later on.

As shown in FIG. 2, the interfering substance removing unit 8 according to this embodiment is provided with the plurality of vibration transmitting members 82. Accordingly, the vibrational energy can be efficiently transmitted to the entire filter 25, and the interfering substance can be removed more appropriately. However, the mode for carrying out the present invention is not limited thereto. The vibrational energy of the piezoelectric element 81 may be transmitted to the filter 25 by using the single vibration transmitting member 82. In this embodiment, the shape or form of the vibration transmitting member 82 is the slender plate-shaped form. However, it is also allowable to adopt any other shape or form. For example, it is also preferable to adopt a slender rod-shaped form. This embodiment is illustrative of such an exemplary case that only one piezoelectric element 81 is arranged on the sensor substrate 21. However, for example, it is also allowable to arrange a plurality of piezoelectric elements 81 so that the piezoelectric elements 81 correspond to the respective vibration transmitting members 82.

In the first embodiment, the recess 21C is formed on the forward end side of the sensor substrate 21, and the detecting unit 22 is arranged in the recess 21C. However, the mode for carrying out the present invention is not limited thereto. That is, even when the recess 21C is not formed, the present invention can be appropriately applied. In this case, for example, a detecting unit 22 may be formed on the forward end side of a flat sensor substrate 21, and a filter 25 may be provided to cover the detecting unit 22 therewith. The effect, which is the same as or equivalent to that of the first embodiment, can be also provided in accordance with the mode as described above. The concerning matter also holds equivalently in relation to other embodiments and modified embodiments described later on.

The first embodiment is illustrative of such an exemplary case that one working electrode 22A and one counter electrode 22B are arranged on the sensor substrate 21 respectively. However, the mode for carrying out the present invention is not limited thereto. It is also allowable that a plurality of detecting units 22 are provided on the sensor substrate 21. Further, a plurality of working electrodes 22A may be provided on the sensor substrate 21, and a plurality of counter electrodes 22B may be provided on the sensor substrate 21. When the plurality of working electrodes 22A are provided on the sensor substrate 21, the measurement of the glucose concentration in the intercellular fluid can be continued even when any malfunction such as any failure or the like arises in one working electrode 22A. Further, when the plurality of counter electrodes 22B are provided on the sensor substrate 21, the measurement of the glucose concentration in the intercellular fluid can be continued even when any malfunction such as any failure or the like arises in one counter electrode 22B. When the plurality of counter electrodes 22B are provided on the sensor substrate 21, it is possible to measure analysis objective items which are different from each other. That is, when the plurality of counter electrodes 22B are provided on the sensor substrate 21, it is possible to measure a plurality of types of specified components contained in a specimen.

First Modified Embodiment

Figure 4:
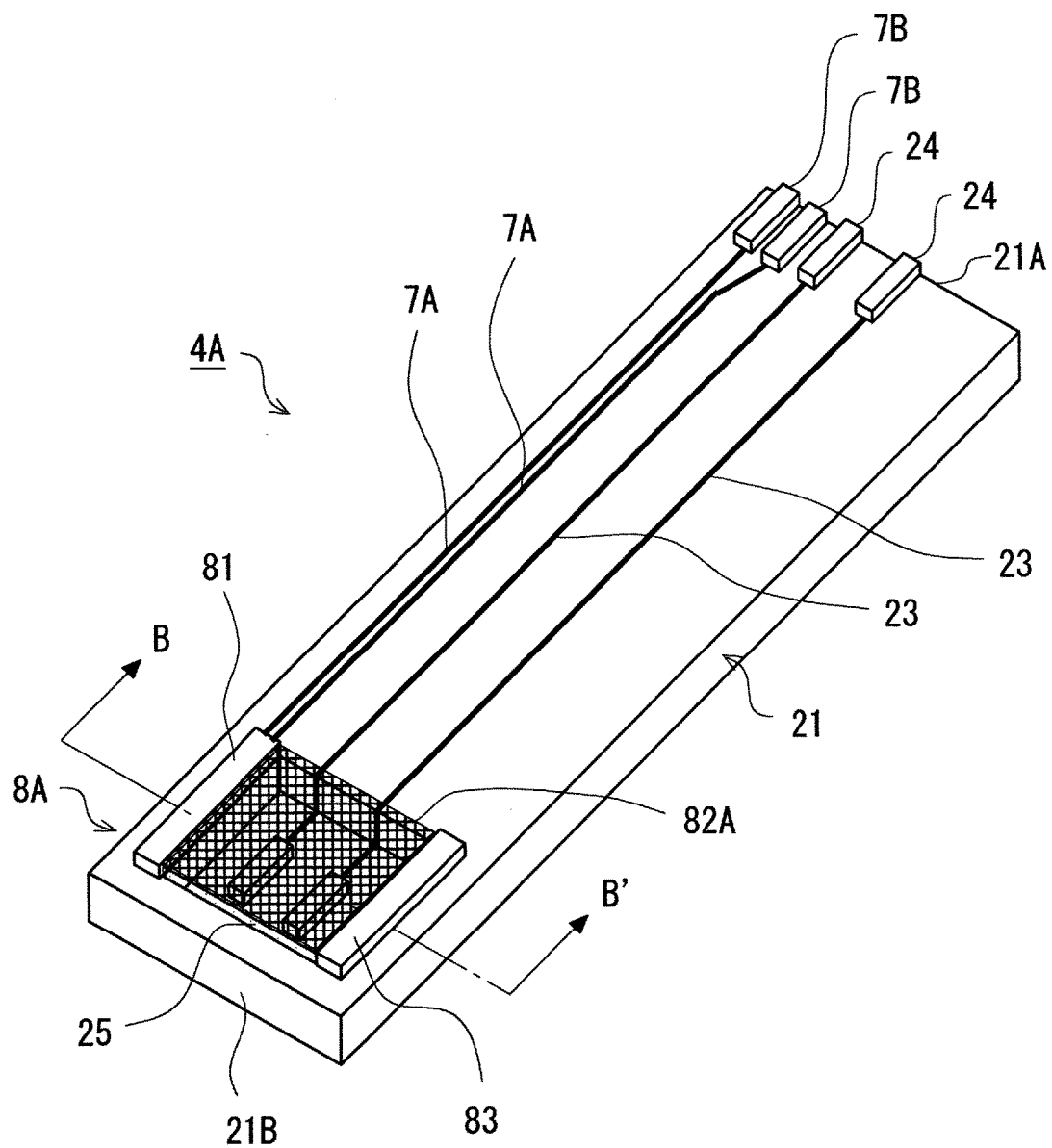
FIG. 4 shows a perspective view illustrating an entire electrochemical sensor according to a first modified embodiment of the first embodiment.

A first modified embodiment of the first embodiment will be explained. FIG. 4 shows a perspective view illustrating an entire electrochemical sensor 4A according to the first modified embodiment of the first embodiment. Reference numeral 8A indicates an interfering substance removing unit according to the first modified embodiment. An electrochemical sensor 4A according to this modified embodiment is constructed in the same manner as in the first embodiment except for the interfering substance removing unit 8A. The interfering substance removing unit 8A also removes the interfering substance accumulated on the filter 25, by vibrating the filter 25. The interfering substance removing unit 8A is constructed to include a piezoelectric element 81, a vibration transmitting member 82A, and a fixed member 83. The members of the electrochemical sensor 4A shown in FIG. 4, which are common to those of the electrochemical sensor 4 of the first embodiment, are designated by the common reference numerals, any detailed explanation of which will be omitted thereby.

Figure 5:
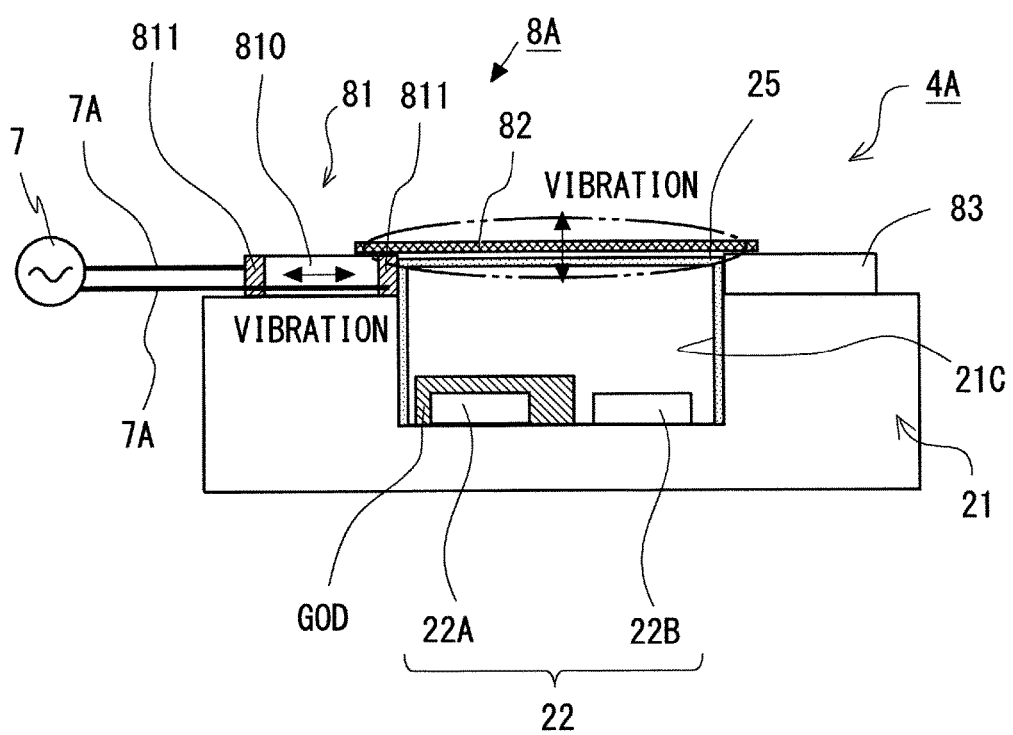
FIG. 5 shows a sectional view taken along a line B-B' indicated by arrows shown in FIG. 4.

FIG. 5 shows a sectional view taken along a line B-B' indicated by arrows shown in FIG. 4. As shown in FIG. 5, the piezoelectric element 81 has two electrodes 811 which are stuck to side surfaces of a piezoelectric member 810. The electrodes 811, 811 are connected to the AC power source 7 via the lead wires 7A and the terminals 7B respectively. The AC voltage is applied from the AC power source 7 to the piezoelectric element 81 constructed as described above. Accordingly, the piezoelectric element 81 repeats the expanding/contracting deformation in the in-plane direction of the sensor substrate 21. In the exemplary arrangement shown in FIG. 5, the piezoelectric element 81 repeats the expanding/contracting deformation in the widthwise direction of the sensor substrate 21.

The vibration transmitting member 82A has a shape different from that of the vibration transmitting member 82 described in the first embodiment. The vibration transmitting member 82A is a planar or sheet-shaped member having a grid (lattice) structure or a mesh structure. The vibration transmitting member 82A has the rigidity to some extent. The fixed member 83 is arranged along the upper end opening edge of the recess 21C so that the fixed member 83 is opposed to the piezoelectric element 81 with the recess 21C intervening therebetween. The fixed member 83 is the immovable member fixed to the sensor substrate 21.

The vibration transmitting member 82A is fixed to the upper surface of the piezoelectric element 81 and the upper surface of the fixed member 83. When the piezoelectric element 81 is vibrated in the widthwise direction of the sensor substrate 21 in accordance with the application voltage from the AC power source 7, the horizontal spacing distance between the piezoelectric element 81 and the fixed member 83 is changed. The rigidity of the vibration transmitting member 82A is relatively high. Therefore, the vibration transmitting member 82A is warped (bent) in the upward-downward direction, and the vibration transmitting member 82A is consequently vibrated in accordance with the change of the horizontal spacing distance as described above (alternate long and two short dashes lines shown in FIG. 5 schematically show the situation in which the vibration transmitting member 82A is vibrated in the upward-downward direction). Accordingly, the vibration transmitting member 82A periodically collides with the filter 25, and the vibrational energy thereof is transmitted to the filter 25. As a result, it is possible to exfoliate the interfering substance adhered to the filter 25, and it is possible to appropriately remove the interfering substance.

In this modified embodiment, the vibration transmitting member 82A is fixed to the upper surfaces of the piezoelectric element 81 and the fixed member 83. However, there is no limitation thereto. For example, the vibration transmitting member 82A may be interposed between the side surface of the piezoelectric element 81 and the side surface of the fixed member 83. Alternatively, the vibration transmitting member 82A may be fixed to the lower surface of the piezoelectric element 81 and the lower surface of the fixed member 83 in such a mode that the vibration transmitting member 82A is interposed with respect to the sensor substrate 21. According to the mode as described above, the horizontal spacing distance between the piezoelectric element 81 and the fixed member 83 is also changed in accordance with the vibration of the piezoelectric element 81, and it is possible to vibrate the vibration transmitting member 82A in the upward-downward direction. It is also allowable that the filter 25 and the vibration transmitting member 82A has an integrated structure. For example, the filter 25 may be formed as a film in the grid or lattice of the vibration transmitting member 82A. Alternatively, the piezoelectric element 81 and the single unit of the filter 25 may be arranged while being brought in contact with each other without using the vibration transmitting member 82A. Accordingly, the vibrational energy of the piezoelectric element 81 may be directly transmitted to the filter 25 thereby, and thus the filter 25 may be vibrated. In the mode for carrying out the present invention, a plurality of piezoelectric elements 81 may be arranged on the sensor substrate 21.

Each of the vibration transmitting member 82 referred to in the first embodiment described above and the vibration transmitting member 82A referred to in the first modified embodiment may be formed as a mesh which is biocompatible, which is prepared by weaving monofilament or multifilament fibers composed of any material including synthetic materials and various organic matters, and which has pores or holes of various dimensions and geometrical forms, in the same manner as a biocompatible mesh structure described, for example, in Japanese Patent Application Laid-Open No. 2004-524059 (P2004-524059A). Specifically, for example, each of the vibration transmitting member 82 and the vibration transmitting member 82A may be formed of polypropylene, polytetrafluoroethylene, polytetrafluoroethylene foam, polyethylene terephthalate, polyglycolic acid, polyglactin, dacron-polythene reinforced silicone, or polyethylene. For example, as described in Japanese Patent Application Laid-Open No. 2010-508897 (P2010-508897A), each of the vibration transmitting member 82 and the vibration transmitting member 82A may be produced by adopting a material which is the same as or equivalent to that of a biocompatible mesh structure composed of a plurality of mutually connected strands provided with a plurality of gaps or interstices formed therebetween.

Second Embodiment

Figure 6:
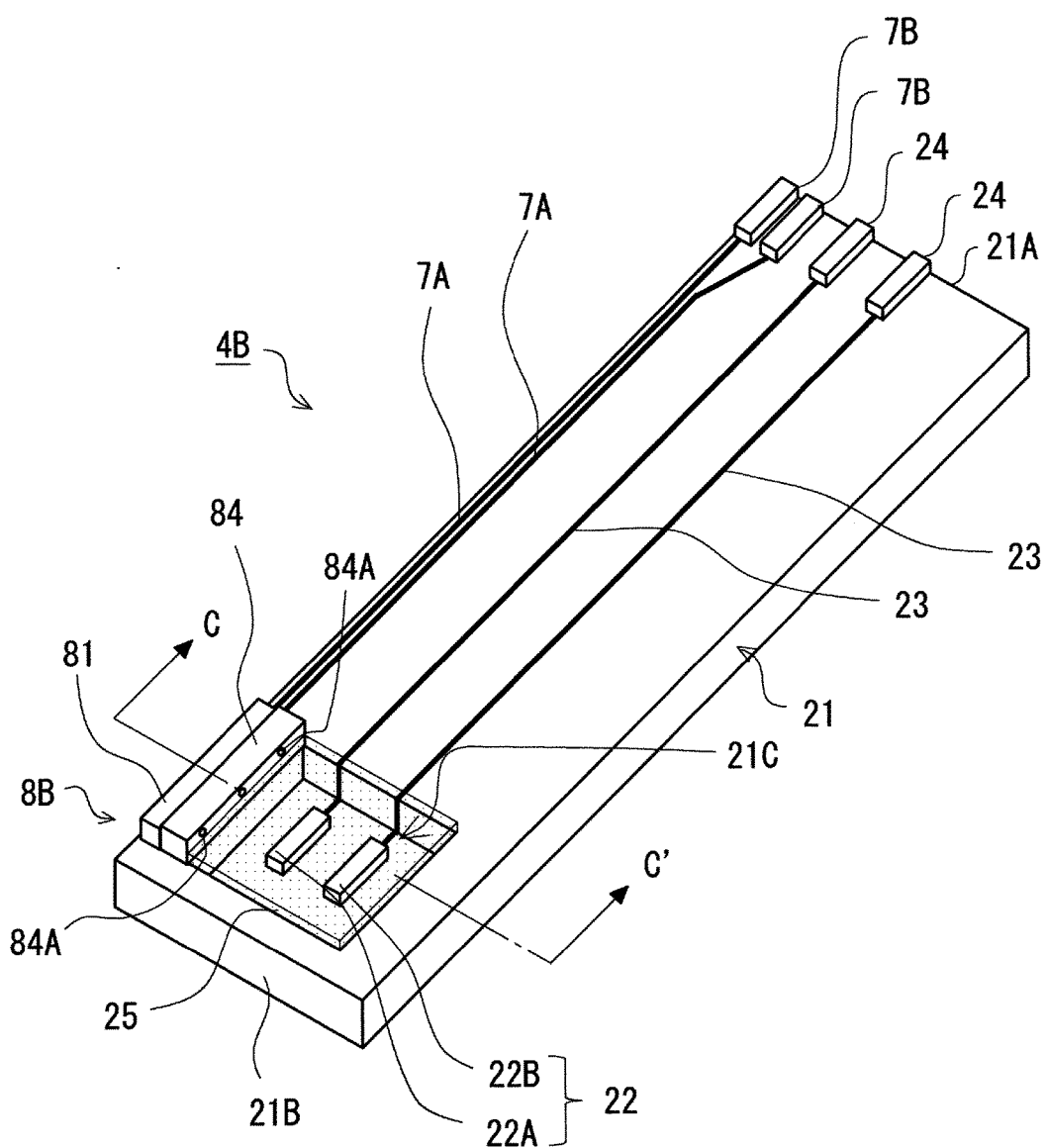
FIG. 6 shows a perspective view illustrating an entire electrochemical sensor according to a second embodiment.

A second embodiment of the electrochemical sensor according to the mode for carrying out the present invention will be explained. FIG. 6 shows a perspective view illustrating an entire electrochemical sensor 4B according to the second embodiment. The members of the electrochemical sensor 4B, which are common to those of the electrochemical sensors 4, 4A, are designated by the common reference numerals, any detailed explanation of which will be omitted thereby. The electrochemical sensor 4B is also provided with an interfering substance removing unit 8B for removing the interfering substance contained in a specimen adhered to the filter 25. The interfering substance removing unit 8B removes the interfering substance adhered to the filter 25 by supplying an agent for decomposing the interfering substance to the filter 25. An explanation will be made below about a specified structure or arrangement of the interfering substance removing unit 8B according to this embodiment.

Figure 7:
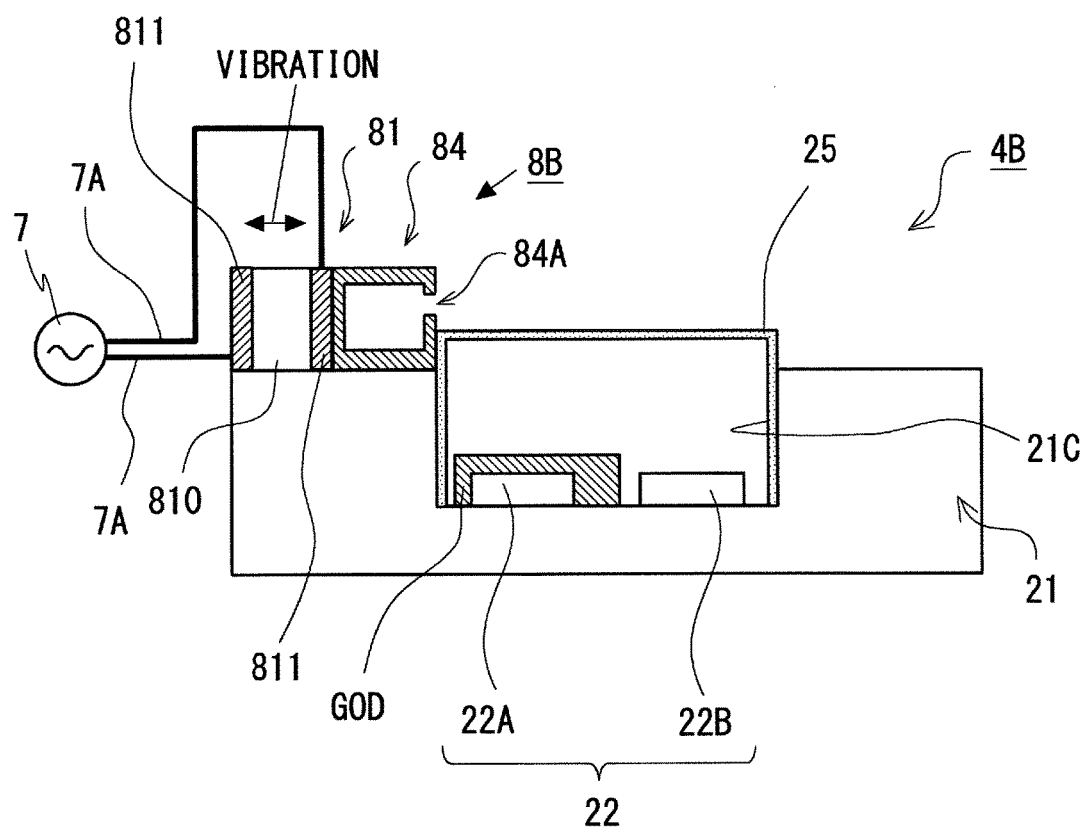
FIG. 7 shows a sectional view taken along a line C-C' indicated by arrows shown in FIG. 6.

FIG. 7 shows a sectional view taken along a line C-C' indicated by arrows shown in FIG. 6. The interfering substance removing unit 8B is constructed by a piezoelectric element 81 and an agent accommodating case 84. The agent accommodating case 84 is the case which accommodates therein an agent for removing the interfering substance. The agent may include, for example, anticoagulant, protease (protein degrading enzyme), and lipase (lipid degrading enzyme). However, any agent other than the above may be accommodated in the agent accommodating case 84.

As shown in FIG. 6, the agent accommodating case 84 is arranged at a position disposed closely to the filter 25 along one upper end opening edge of the recess 21C. Discharge holes 84A are formed to be open on the agent accommodating case 84 in order that the agent stored therein is discharged toward the filter 25 as described later on. The plurality (three in this embodiment) of discharge holes 84A are formed for the agent accommodating case 84 in the longitudinal direction of the sensor substrate 21. The respective discharge holes 84A confront the filter 25 which covers the recess 21C.

The surface of the agent accommodating case 84, on which the discharge holes 84A are formed, is referred to as "front surface", and the surface, which is disposed on the side opposite thereto, is referred to as "back surface". The piezoelectric element 81 is provided on the sensor substrate 21 so that the piezoelectric element 81 is brought in contact with the back surface of the agent accommodating case 84. The piezoelectric element 81 is constructed by a piezoelectric member 810, and two electrodes 811, 811 which interpose the piezoelectric member 810 on side surfaces thereof, in the same manner as in the first embodiment. The respective electrodes 811, 811 are connected to the AC power source 7 via lead wires 7A and terminals 7B. The AC voltage is applied from the AC power source 7 to the piezoelectric element 81 in the same manner as in the other embodiments.

When the AC voltage is applied to the piezoelectric element 81 by the AC power source 7, the piezoelectric element 81 is vibrated in the horizontal direction in relation to the sensor substrate 21. In this arrangement, the back surface of the agent accommodating case 84 abuts against the side surface of the piezoelectric element 81. Therefore, the vibrational energy of the piezoelectric element 81 is transmitted to the agent accommodating case 84, and the back surface is pressed. As a result, the agent accommodating case 84 is vibrated, and the agent, which is stored therein, is discharged from the discharge holes 84A toward the filter 25. As a result, the agent contained in the agent accommodating case 84 is sprinkled onto the filter 25. Accordingly, the interfering substance, which adheres to the filter 25, is decomposed and removed. For example, the protein, which is accumulated on the filter, is degraded by protease, and the lipid is degraded by lipase.

According to the electrochemical sensor 4B of this embodiment, the fresh agent, which is prepared to remove the interfering substance, can be supplied to the filter 25 at any time during the measurement duration period (for example, during the subcutaneous retention period). Accordingly, the interfering substance can be removed more efficiently as compared with a case in which the filter 25 is previously impregnated with the agent.

This embodiment is illustrative of such an exemplary case that the three discharge holes 84A are formed through the agent accommodating case 84. However, it is a matter of course that the number thereof may be changed. The number may be determined on the basis of the parameter including, for example, the surface area of the filter 25, the cross-sectional area of the discharge hole 84A, and the voltage applied to the piezoelectric element 81. Alternatively, the interior of the agent accommodating case 84 may be comparted into a plurality of accommodating chambers. In this case, agents of different types may be accommodated in the respective accommodating chambers. Further alternatively, a plurality of agent accommodating cases 84 may be arranged on the sensor substrate 21 so that the filter 25 is surrounded thereby.

Figure 8:
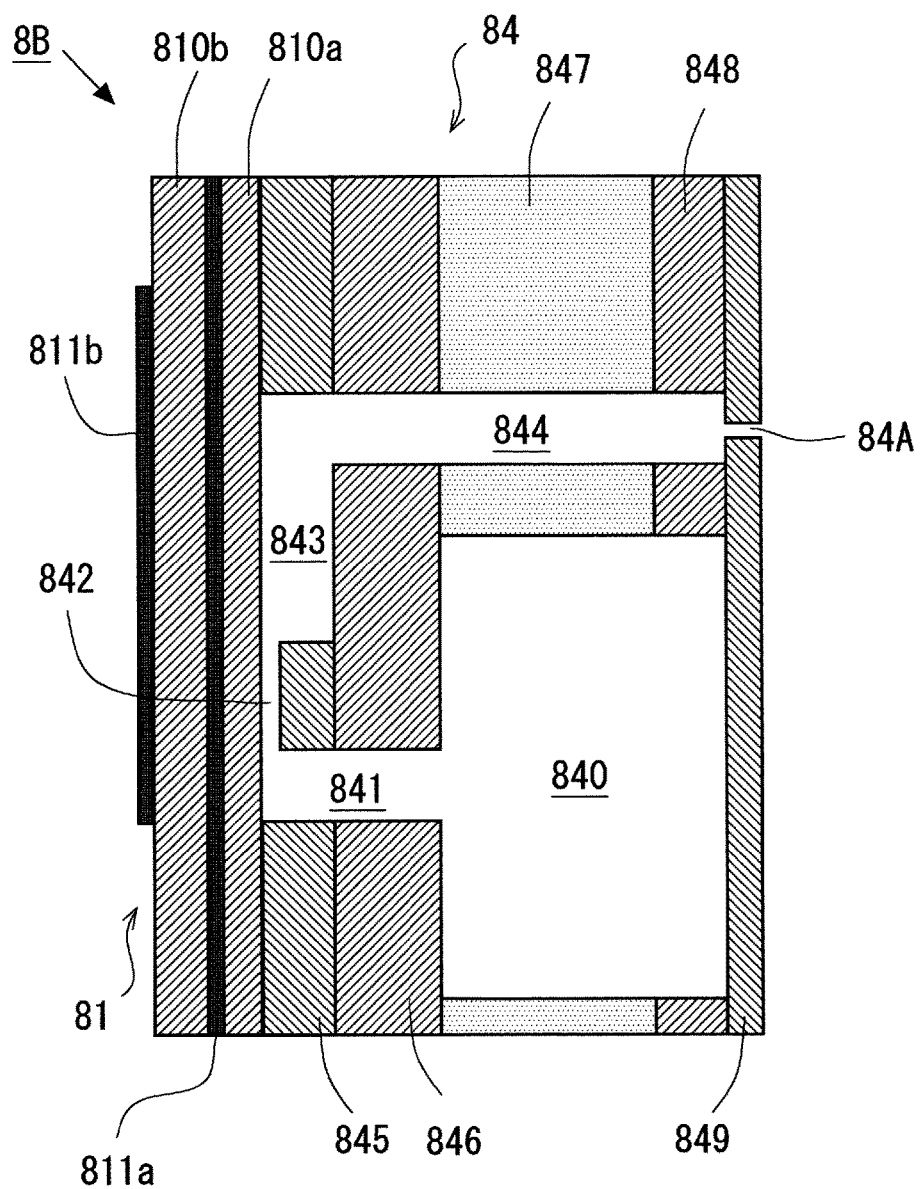
FIG. 8 shows an exemplary detailed arrangement of an agent accommodating case and a piezoelectric element of an interfering substance removing unit according to the second embodiment.

An explanation will now be made about an exemplary detailed arrangement of the agent accommodating case 84 and the piezoelectric element 81. FIG. 8 shows the exemplary detailed arrangement of the agent accommodating case 84 and the piezoelectric element 81 of the interfering substance removing unit 8B. The agent accommodating case 84 and the piezoelectric element 81 according to this embodiment can be constructed in the same manner as a liquid discharge head described, for example, in Japanese Patent Application Laid-Open No. 2011-25632A (P2011-25632A).

In the exemplary case shown in the drawing, the piezoelectric element 81 is provided on the back surface side of the agent accommodating case 84. An agent accommodating portion 840, which is a hollow space capable of accommodating the agent, is formed at the inside of the agent accommodating case 84. The discharge hole 84A, from which the agent is discharged to the outside, is formed on a front surface wall of the agent accommodating case 84. The agent accommodating portion 840 and the discharge hole 84A are communicated with each other via a first agent supply flow passage 841, a throttle 842, a liquid pressurizing chamber 843, and a second agent supply flow passage 844. The back surface of the agent accommodating case 84 forms an opening. The opening is closed by the piezoelectric element 81 which is adhered to the agent accommodating case 84.

As shown in the drawing, the agent accommodating case 84 has a stacked structure which is constructed by stacking a plurality of plates. The plates are a cavity plate 845, a supply plate 846, an accommodating plate 847, a cover plate 848, and a nozzle plate 849 as referred to in this order starting from the side of the piezoelectric element 81. A large number of holes are formed for the plates. The respective plates 845 to 849 are stacked by the aid of adhesive layers so that the respective holes are communicated with each other. Thus, for example, the agent accommodating portion 840, the first agent supply flow passage 841, the throttle 842, the liquid pressurizing chamber 843, the second agent supply flow passage 844, and the discharge hole 84A are formed. In the exemplary structure shown in FIG. 8, the liquid pressurizing chamber 843 approximately has a depth thereof of 10 to 200 μm, a width of 100 to 1000 μm, and a length of 200 to 2000 μm. The throttle 842 approximately has a depth thereof of 0.05 to 1 μm, a width of 100 to 1000 μm, and a length of 10 to 100 μm. However, there is no limitation to the sizes or dimensions described above.

As for the plates 845 to 849 as described above, the plates may be manufactured, for example, by means of the rolling method. After that, the holes, which are to be formed into the agent accommodating portion 840, the first agent supply flow passage 841, the liquid pressurizing chamber 843, the second agent supply flow passage 844, and the discharge hole 84A, may be processed to have predetermined shapes by means of the etching, and the portion, which is to be formed into the throttle 842, may be manufactured by means of the half etching. Each of the plates 845 to 849 may be formed of at least one metal selected from the group consisting of those based on Fe—Cr, Fe—Ni, and WC—TiC.

In the next place, the piezoelectric element 81 has the stacked structure composed of piezoelectric ceramic layers 810a, 810b which are two piezoelectric members. Each of the piezoelectric ceramic layer 810a, 810b has a thickness of about 20 μm. Therefore, the entire piezoelectric element 81 has a thickness of about 40 μm. Each of the piezoelectric ceramic layer 810a, 810b is composed of, for example, a ceramics material based on lead zirconate titanate (PZT) having the ferroelectric property.

The piezoelectric element 81 has a first electrode 811a which is composed of a metal material such as those based on Ag—Pd or the like and a second electrode 811b which is composed of a metal material such as those based on Au or the like. In this exemplary arrangement, the piezoelectric ceramic layer 810a, the first electrode 811a, the piezoelectric ceramic layer 810b, and the second electrode 811b are provided in this order as referred to from those disposed nearer to the back surface of the agent accommodating case 84. In other words, the first electrode 811a and the second electrode 811b are arranged so that only the piezoelectric ceramic layer 810b, which is positioned on the outer side, is interposed. The area of the piezoelectric ceramic layer 810b, which is interposed by the second electrode 811b and the first electrode 811a, is referred to as "active portion". The piezoelectric ceramic material, which is disposed at the concerning portion, is polarized. In the case of the piezoelectric element 81 of this exemplary arrangement, only the piezoelectric ceramic layer 810b, which is disposed on the outer side, includes the active portion. The piezoelectric ceramic layer 810a does not include any active portion, which functions as a vibration plate. Therefore, the piezoelectric element 81 has the so-called unimorph type structure.

The piezoelectric element 81 and the agent accommodating case 84, which are constructed as described above, are adhered to one another, for example, by the aid of an adhesive layer. As for the adhesive layer, it is also allowable to use an adhesive of, for example, a thermosetting resin such as epoxy resin, phenol resin, polyphenylene ether resin or the like.

As shown in FIG. 7 as well, the first electrode 811a and the second electrode 811b are connected to the AC power source 7 via the lead wires 7A and the terminals 7B. The AC voltage from the AC power source 7 is applied to the piezoelectric element 81. When the voltage is applied to the piezoelectric ceramic layer 810b in the polarization direction thereof while allowing the second electrode 811b to have an electric potential different from that of the first electrode 811a, the portion, to which the voltage is applied, functions as the active portion which is strained in accordance with the piezoelectric effect. In this situation, the piezoelectric ceramic layer 810b is expanded or contracted in the thickness direction, i.e., in the stacking direction, and the piezoelectric ceramic layer 810*b* is contracted or expanded in the direction perpendicular to the stacking direction, i.e., in the in-plane direction in accordance with the piezoelectric transversal (lateral) effect. On the other hand, the remaining piezoelectric ceramic layer 810*a* is the inactive layer which does not have any area interposed by the second electrode 811*b* and the first electrode 811*a*. Therefore, the remaining piezoelectric ceramic layer 810*a* is not deformed spontaneously. That is, the piezoelectric ceramic layer 810*a*, which is the inactive layer, is not affected by the electric field. Therefore, the piezoelectric ceramic layer 810*a* is not shrunk spontaneously, and the piezoelectric ceramic layer 810*a* intends to regulate the deformation of the active portion. As a result, the difference arises in the strain in the polarization direction between the piezoelectric ceramic layer 810*b* and the piezoelectric ceramic layer 810*a*. The piezoelectric ceramic layer 810*b* is deformed (subjected to the unimorph deformation) so that the piezoelectric ceramic layer 810*b* protrudes toward the liquid pressurizing chamber 843.

An explanation will be made about the specified control contents provided when the agent, which is accommodated in the agent accommodating case 84, is discharged from the discharge hole 84A. As for the control contents, the second electrode 811*b* is previously allowed to have the electric potential (hereinafter referred to as "high electric potential") higher than that of the first electrode 811*a*. The second electrode 811*b* is once allowed to have the same electric potential (hereinafter referred to as "low electric potential") as that of the first electrode 811*a* every time when the discharge request is given. After that, the second electrode 811*b* is allowed to have the high electric potential again at a predetermined timing. Accordingly, the piezoelectric ceramic layers 810*a*, 810*b* are returned to the original shapes at a timing at which the second electrode 811*b* is allowed to have the low electric potential. The volume of the liquid pressurizing chamber 843 is increased as compared with the initial state (state in which the electric potentials of the both electrodes are different from each other). In this situation, the negative pressure is applied to the interior of the liquid pressurizing chamber 843, and the agent is sucked into the liquid pressurizing chamber 843 from the side of the agent accommodating portion 840.

After that, the piezoelectric ceramic layers 810*a*, 810*b* are deformed so that the piezoelectric ceramic layers 810*a*, 810*b* protrude toward the liquid pressurizing chamber 843 at a timing at which the second electrode 811*b* is allowed to have the high electric potential again. The pressure in the liquid pressurizing chamber 843 is the positive pressure on account of the decrease in the volume of the liquid pressurizing chamber 843, and the agent is discharged from the discharge hole 84A. The electric power application, which is effected by the AC power source 7, is controlled as described above. Accordingly, the agent can be sprinkled onto the filter 25 from the discharge hole 84A at the desired timing. It is possible to decompose and remove the interfering substance adhered to the filter 25.

In the exemplary arrangement shown in FIG. 8, the liquid pressurizing chamber 843 approximately has a depth thereof of 10 to 200 µm, a width of 100 to 1000 µm, and a length of 200 to 2000 µm. The throttle 842 approximately has a depth thereof of 0.05 to 1 µm, a width of 100 to 1000 µm, and a length of 10 to 100 µm. However, there is no limitation to the dimensions or sizes described above.

It is a matter of course that the structure, the constitutive materials, and other features of the piezoelectric element 81, which have been described with reference to FIG. 8, can be appropriately applied to any piezoelectric element 81 of any other embodiment.

Third Embodiment

Figure 9:
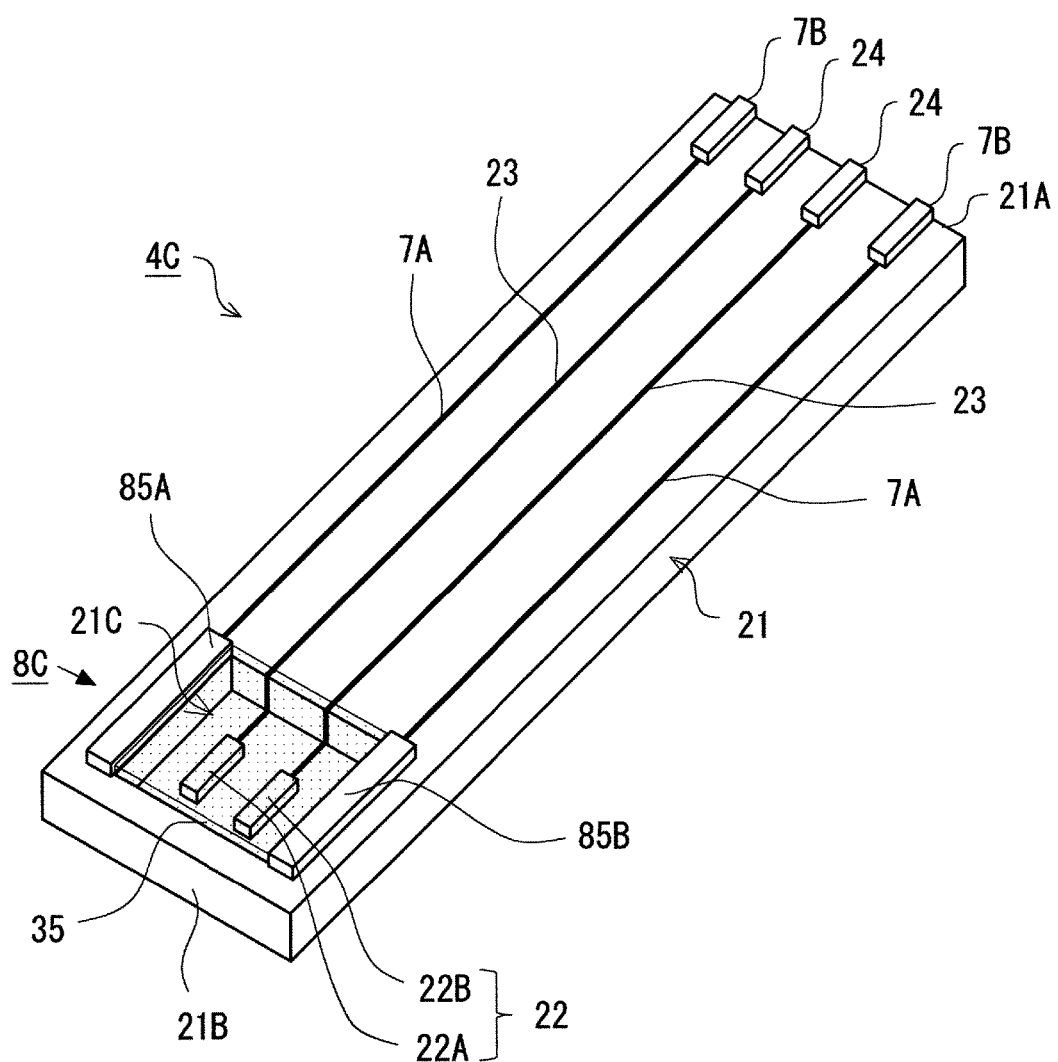
FIG. 9 shows a perspective view illustrating an entire electrochemical sensor according to a third embodiment.

An explanation will be made about a third embodiment of the electrochemical sensor according to the mode for carrying out the present invention. FIG. 9 shows a perspective view illustrating an entire electrochemical sensor 4C according to the third embodiment. The members of the electrochemical sensor 4C, which are common to those of the electrochemical sensors 4, 4A, 4B, are designated by the common reference numerals, any detailed explanation of which will be omitted thereby. The electrochemical sensor 4C is also provided with an interfering substance removing unit 8C which is provided to remove the interfering substance collected on a filter.

The filter 35 according to this embodiment is the same as or equivalent to the filter 25 in that the filter 35 has the function to permit the permeation of glucose as the specified objective substance on one hand and regulate the permeation of the interfering substance on the other hand. The filter 35 is constructed so that the internal electrical resistance thereof is higher than the electrical resistance of a specimen (intercellular fluid in this case). In this embodiment, the filter 35 is composed of an insulator or insulating material. The filter 35 can be formed by using, for example, ceramics, glass, or synthetic resin.

The interfering substance removing unit 8C is provided with a pair of removing process electrodes 85A, 85B which are used in order that the interfering substance adhered to the filter 35 is removed from the filter 35. The removing process electrodes 85A, 85B are provided on the sensor substrate 21. The removing process electrodes 85A, 85B are arranged in such a state that the filter 35 is interposed from the both sides thereof and the removing process electrodes 85A, 85B are brought in contact with the filter 35. As shown in the drawing, the removing process electrodes 85A, 85B are provided to extend along a pair of opposing upper end opening edges of the recess 21C. The removing process electrodes 85A, 85B are connected to the AC power source 7 via the lead wires 7A and the terminals 7B. The removing process electrodes 85A, 85B are, for example, platinum electrodes. However, the material for the removing process electrodes 85A, 85B is not limited thereto.

The filter 35, which is interposed between the removing process electrodes 85A, 85B, is an insulator. Therefore, when the AC voltage is applied between the removing process electrodes 85A, 85B by means of the AC power source 7, the electricity flows along such a route that the electrical resistance is lower and the route length is shorter. In this embodiment, the filter 35 is interposed between the removing process electrodes 85A, 85B. In this situation, the electricity may highly possibly flow along the surface of the filter 35 when the voltage is applied between the removing process electrodes 85A, 85B by means of the AC power source 7.

In the meantime, the intercellular fluid can be grasped as the electrolyte. Therefore, when the voltage is applied between the removing process electrodes 85A, 85B immersed in the intercellular fluid, the removing process electrodes 85A, 85B are subjected to the electrolysis. That is, the interfering substance, which adheres to the removing process electrodes 85A, 85B, is removed in accordance with the action of the electrolytic cleaning. This action will be described in more detail below. When the voltage is applied between the removing process electrodes 85A, 85B, then the negative ion is attracted to the anode, and the electron is deprived from the intercellular fluid to cause the oxidation. On the other hand, the positive ion is attracted to the cathode, and thus the electron is given to the intercellular fluid to cause the reduction. The removing process electrodes 85A, 85B are subjected to the electrolysis in accordance with the chemical action of oxidation/reduction as described above. Oxygen gas is produced locally (microscopically) from the anode, and hydrogen gas is produced locally from the cathode.

In the case of the interfering substance removing unit 8C of this embodiment, the interfering substance, which adheres to the removing process electrodes 85A, 85B, is exfoliated by utilizing the physical effect caused by the force of the bubble of the gas generated from the removing process electrodes 85A, 85B, for example, the agitating action caused by the gas. In this arrangement, the respective removing process electrodes 85A, 85B are arranged in such a mode that they are brought in contact with the filter 35. Therefore, the interfering substance, which adheres to the removing process electrodes 85A, 85B and the filter 35, is joined or linked together and formed as a set. For example, the interfering substance, which adheres to the removing process electrodes 85A, 85B and the filter 35, is joined or linked together to form the foreign body capsule (FBC). In other words, in the electrochemical sensor 4C of this embodiment, the removing process electrodes 85A, 85B and the filter 35 are arranged while being brought in contact with each other so that the interfering substance, which adheres to the removing process electrodes 85A, 85B and the filter 35, is formed while being joined or linked (connected) together.

Therefore, when the interfering substance is exfoliated from the removing process electrodes 85A, 85B by performing the electrolytic cleaning with respect to the removing process electrodes 85A, 85B as described above, the interfering substance is also exfoliated from the filter 35 in cooperation therewith. In this way, it is possible to remove the interfering substance adhered to the filter 35, i.e., it is possible to remove the foreign body capsule (FBC) formed on the filter 35, in cooperation with the electrolytic cleaning for the removing process electrodes 85A, 85B.

Further, in this embodiment, the AC voltage from the AC power source 7 is applied to the removing process electrodes 85A, 85B. Therefore, the both polarities are alternated in a pulsed manner. Therefore, the cleaning efficiency is improved for the removing process electrodes 85A, 85B, and the interfering substance, which adheres to the filter 35, can be finally removed more efficiently. In the electrochemical sensor 4C of this embodiment, the removing process electrodes 85A, 85B and the filter 35 are arranged while being brought in contact with each other. However, the mode for carrying out the present invention is not limited thereto. The removing process electrodes 85A, 85B and the filter 35 may be arranged while being disposed closely to one another, provided that the arrangement is in such a mode that the interfering substance, which adheres to the removing process electrodes 85A, 85B and the filter 35, is formed while being joined or linked together.

The present invention has been explained above. However, the techniques, which relate to the electrochemical sensor according to the present invention, are not limited thereto. It is possible to include combinations thereof as far as possible. Various changes or modifications may be applied or added to the embodiments described above within a range without deviating from the gist or essential characteristics of the present invention. For example, the present invention is applicable to any sensor other than the electrochemical sensor. The present invention may be applied, for example, to a sensor of such a type that a color developing reagent enzyme, which specifically causes the reaction of an objective substance, is previously retained in a detecting unit for detecting the objective substance contained in a sample, and the objective substance is measured in accordance with the colorimetric method for measuring the intensity at a color developing wavelength by means of an optical device or apparatus.

PARTS LIST

1: component continuous measuring apparatus, 2: casing, 3: circuit board, 4, 4A, 4B, 4C: electrochemical sensor, 5: adhesive film, 6: skin, 7: AC power source, 8, 8A, 8B, 8C: interfering substance removing unit, 21: sensor substrate, 21C: recess, 22: detecting unit, 22A: working electrode, 22B: counter electrode, 25, 35: filter, 81: piezoelectric element, 82: vibration transmitting member, 83: fixed member, 84: agent accommodating case, 84A: discharge hole.

The invention claimed is:

1. A sensor for measuring an objective substance present in a sample, the sensor comprising:
   a substrate;
   a detecting unit provided on the substrate and configured to detect an objective substance present in a sample, where the sample is a body fluid;
   a filter covering the detecting unit and configured to permit permeation of the objective substance while also configured to regulate permeation of an interfering substance present in the sample; and
   a removing unit configured to remove the interfering substance adhered to the filter by vibrating the filter,
   wherein a portion of the sensor is implanted subcutaneously.

2. The sensor according to claim 1, wherein the removing unit comprises:
   a piezoelectric element which is vibrated by application of a voltage to the piezoelectric element; and
   a vibration transmitting unit fixed to the piezoelectric element and configured to transmit the vibrational energy of the piezoelectric element to the filter.

3. The sensor according to claim 1, wherein the objective substance is selected from the group consisting of glucose, lactic acid and bile acid.

4. The sensor according to claim 1, wherein the objective substance is glucose.

5. The sensor according to claim 1, wherein the detecting unit comprises a reagent enzyme.

6. The sensor according to claim 5, wherein the reagent enzyme is glucose dehydrogenase or glucose oxidase.

7. A method for removing an interfering substance from a filter of a sensor, where the sensor further comprises a detecting unit provided on a substrate and configured to detect an objective substance present in a sample where the sample is a body fluid, the method comprising:
   allowing the interfering substance to adhere to the filter by covering the detecting unit with the filter which permits permeation of the objective substance and which also regulates permeation of the interfering substance present in the sample, and
   then removing the interfering substance adhered to the filter by treatment with a removing unit configured to remove the interfering substance by vibrating the filter.

8. The method according to claim 7, wherein the removing unit comprises:
a piezoelectric element which is vibrated by application of a voltage to the piezoelectric element; and
a vibration transmitting unit fixed to the piezoelectric element and configured to transmit the vibrational energy of the piezoelectric element to the filter.

9. The method according to claim 7, wherein a portion of the sensor is implanted subcutaneously.

10. The method according to claim 7, wherein the objective substance is selected from the group consisting of glucose, lactic acid and bile acid.

11. The method according to claim 7, wherein the objective substance is glucose.

12. The method according to claim 7, wherein the detecting unit comprises a reagent enzyme.

13. The method according to claim 12, wherein the reagent enzyme is glucose dehydrogenase or glucose oxidase.

* * * * *